United States Patent

Freidberg

(10) Patent No.: US 6,254,627 B1
(45) Date of Patent: Jul. 3, 2001

(54) NON-THROMBOGENIC STENT JACKET

(75) Inventor: Carlos Vonderwalde Freidberg, Mexico City (MX)

(73) Assignee: Diseno y Desarrollo Medico S.A. de C.V., Mexico City (MX)

( * ) Notice: Subject to any disclaimer, the term of this patent is extended or adjusted under 35 U.S.C. 154(b) by 0 days.

(21) Appl. No.: 09/156,034

(22) Filed: Sep. 17, 1998

Related U.S. Application Data

(63) Continuation-in-part of application No. 08/935,784, filed on Sep. 23, 1997, and a continuation-in-part of application No. 09/005,972, filed on Jan. 12, 1998, and a continuation-in-part of application No. 09/035,114, filed on Mar. 4, 1998, and a continuation-in-part of application No. 09/053,200, filed on Apr. 1, 1998, now abandoned.

(51) Int. Cl.[7] .................................... A61F 2/06
(52) U.S. Cl. ................ 623/1.11; 623/1.13; 623/23.72; 606/195
(58) Field of Search ............... 623/1, 1.11, 1.13, 623/1.14, 1.23, 1.44, 1.27, 23.72, 23.7; 606/153, 194, 195

(56) References Cited

U.S. PATENT DOCUMENTS

| 4,400,833 | 8/1983 | Kurland ................. 3/1 |
| 4,502,159 | 3/1985 | Woodroof et al. ........ 3/1.4 |
| 4,801,299 | * 1/1989 | Brendel et al. ........... 623/1 |
| 5,383,928 | 1/1995 | Scott et al. ............. 623/1 |
| 5,489,298 | 2/1996 | Love et al. ............. 623/2 |
| 5,512,291 | 4/1996 | Li ..................... 424/443 |
| 5,549,663 | 8/1996 | Cottone, Jr. ............. 623/1 |
| 5,556,414 | 9/1996 | Turi ................... 606/198 |
| 5,571,173 | 11/1996 | Parodi ................... 623/1 |
| 5,575,818 | 11/1996 | Pinchuk ................. 623/1 |
| 5,584,876 | 12/1996 | Bruchman et al. ......... 623/1 |
| 5,599,307 | 2/1997 | Bacher et al. ........... 604/101 |
| 5,628,786 | 5/1997 | Banas et al. ............. 623/1 |
| 5,641,373 | 6/1997 | Shannon et al. ......... 156/242 |
| 5,653,743 | 8/1997 | Martin ................... 623/1 |
| 5,653,747 | 8/1997 | Dereume ................. 623/1 |
| 5,667,523 | 9/1997 | Bynon et al. ........... 606/198 |
| 5,674,298 | 10/1997 | Levy et al. ............. 8/94.11 |
| 5,693,085 | 12/1997 | Buirge et al. ........... 623/1 |
| 5,707,385 | 1/1998 | Williams ............... 606/192 |
| 5,723,004 | 3/1998 | Dereume et al. ......... 623/1 |
| 5,741,326 | * 4/1998 | Solovay ................. 623/1 |
| 5,782,914 | 7/1998 | Schankereli ............. 623/11 |
| 5,934,283 | * 8/1999 | Willem et al. ........... 128/885 |
| 5,980,565 | * 11/1999 | Jayaraman .............. 623/1 |
| 5,997,573 | * 12/1999 | Quijano et al. .......... 623/1 |
| 6,117,166 | * 9/2000 | Winston et al. .......... 623/1.13 |

FOREIGN PATENT DOCUMENTS

| 0 839 506 | 5/1998 | (EP) . |
| WO 94/15583 | 7/1994 | (WO) . |
| WO 97/09006 | 3/1997 | (WO) . |
| WO 97/12563 | 4/1997 | (WO) . |
| WO 97/24081 | 7/1997 | (WO) . |

\* cited by examiner

*Primary Examiner*—Paul B. Prebilic
(74) *Attorney, Agent, or Firm*—Heller Ehrman White & McAuliffe LLP

(57) ABSTRACT

A jacketed stent assembly comprising a tubular, expandable stent, preferably having a metallic framework, jacketed with a cylinder of biocompatible, non-thrombogenic expandable material, such as heterologous tissue, which, in a preferred embodiment, contains a therapeutic or diagnostic agent. In a preferred embodiment, the jacket of the expandable stent is formed of bovine or porcine pericardial tissue. A delivery catheter having an expandable member on its distal extremity may be used to deliver the stent assembly to a desired region in a lumen of a patient. The jacketed stent is expanded to be seated within the body lumen. Self-expanding jacketed stents are also contemplated

32 Claims, 3 Drawing Sheets

NON-THROMBOGENIC STENT JACKET

RELATED APPLICATIONS

This application is a continuation-in-part application of application Ser. No. 08/935,784, filed Sep. 23, 1997, entitled STENT COVERED WITH HETEROLOGOUS TISSUE, and application Ser. No. 09/005,972, filed Jan. 12, 1998, entitled STENT WITH A BIOCOMPATIBLE NON-THROMBOGENIC JACKET, and application Ser. No. 09/035,114, filed Mar. 4, 1998, entitled NON-THROMBOGENIC STENT JACKET CONTAINING THERAPEUTIC AGENTS, and application Ser. No. 09/053,200, filed Apr. 1, 1998, entitled NON-THROMBOGENIC STENT JACKET (abandoned), which are incorporated herein in their entirety.

BACKGROUND OF THE INVENTION

This invention relates to the field of expandable intraluminal support devices such as stents and the like. Typically, stents are expandable, tubular metallic devices that are positioned within a patient's vasculature or other body lumen and expanded in order to support a vessel or body lumen at a desired intraluminal location to allow the flow of blood or other body fluids therethrough. Often, the stents are formed from a deformable metal and delivered to the desired intraluminal location by mounting the stent onto an expandable portion, e.g. a balloon, on the distal extremity of a delivery catheter. By advancing the catheter through the body lumen, the stent may be delivered to a desired position and expanded therein by expanding the expandable member, e.g. the balloon to an expanded configuration, seating it within the artery or other body lumen. Other implementations make use of a self-expanding stent formed from a suitable material such as pseudoelastic material that is delivered in a constricted condition and when released spontaneously expands to an enlarged configuration. In other embodiments, a stent made of shape memory alloy (e.g. NiTi alloy) may be inserted into the body lumen in a martensitic phase and transformed to an austenite phase which has an expanded memory when raised to a temperature above the transformation temperature, usually less than 45° C.

Stents are often used in conjunction with an intravascular treatment for obstructive coronary artery disease. For example, ablation, atherectomy, balloon dilation, laser treatment or other procedures are among the method used to widen a stenotic region of a patient's vasculature. However, restenosis occurs in large percentage of percutaneous transluminal coronary angioplasty (PTCA) patients and rates can be even higher with other procedures. The prior art has employed a number of mechanical and pharmacological strategies to reduce the restenosis rate, but none have been particularly effective. Accordingly, stents have been proposed to maintain the patency of a treated vessel and prevent restenosis. Using stents, restenosis rates have fallen to less than 20%.

Restenosis is thought to be a natural healing reaction provoked by injury from the intravascular procedure. The healing process frequently causes thrombosis and may lead to intimal hyperplasia that occludes the vessel. Although helpful in reducing restenosis, stents do not represent a complete solution. The framework of the stent may still allow migration and proliferation of the smooth muscle cells, while the stent itself can be thrombogenic. To address these problems, stents have been covered with DACRON, PTFE and autologous vein and the stent surface has been seeded with endothelial cells or otherwise treated. Each of these solutions suffer from certain drawbacks, such as not being biocompatible, lacking sufficient mechanical strength, having a surface that is difficult to prepare, lack of ready availability and being thrombogenic. Antithrombotic drug regimens, in which anticoagulants and thrombolytic agents are administered during and after deployment of the stent, have also been employed to reduce the risk of thrombosis.

Thus, there remains a need for a stent capable of minimizing restenosis while having a consistency similar to the native artery, a non-thrombogenic surface and sufficient mechanical strength as well as being biocompatible and readily available. This invention satisfies these and other needs.

SUMMARY OF THE INVENTION

The invention is directed to a stent assembly suitable for maintaining the patency of a bodily lumen, generally comprising an expandable stent and an expandable, biocompatible, non-thrombogenic jacket such as heterologous tissue disposed about the exterior of the expandable stent. Preferably, the heterologous tissue is selected from the group consisting of bovine pericardium, porcine pericardium, aortic leaflet and other suitable heterologous tissue. The stent may be an expandable, tubular framework and may be a conventional self expanding or balloon expandable stent. The jacket is disposed about either or both of the outer and inner surfaces of the stent. In a preferred embodiment, the jacket is generally cylindrical for corresponding to the tubular framework or the stent.

This invention is also directed to a method for maintaining the patency of a bodily lumen generally comprising providing a delivery catheter having an expandable member on the distal extremity thereof, mounting the stent assembly, including a tubular stent with a jacket of biocompatible, non-thrombogenic expandable material such as heterologous tissue disposed about at least part of the stent, on the expandable member on the distal extremity of the delivery catheter. The catheter is advanced through the body lumen within the patient until the distal extremity of the catheter having the stent assembly is positioned at a desired location therein. The stent assembly is expanded by expanding the expandable member onto which the stent assembly is mounted to anchor the stent assembly within the body lumen. Once the stent assembly is effectively positioned within the body lumen, the expanded expandable member may be contracted, e.g. by deflating the balloon, and then the delivery catheter may be withdrawn.

A presently preferred embodiment of the invention is directed to a stent assembly suitable for expansion within a body lumen and delivery of a therapeutic or diagnostic agent therein, generally comprising an expandable stent and an expandable, biocompatible, non-thrombogenic jacket such as heterologous tissue, which contains the therapeutic or diagnostic agent and which is disposed about the expandable stent. The jacket releasably contains at least one therapeutic or diagnostic agent.

A wide variety of therapeutic or diagnostic agents for a variety of indications can be used, including angiogenesis agents and antithrombotic agents. The term "antithrombotic agents" is meant to include various agents for reducing the risk of thrombosis, including anticoagulants such as heparin, thrombolytic agents such as urokinase, streptokinase, tissue plasminogen activator (ACTILYSE), monoclonal antibodies such as abciximab (REOPRO), fibrinolytic agents, and the like. Angiogenesis agents that stimulate the growth of neovessels include agents such as basic Fibroblast Growth Factor (bFGF) and Vascular Endothelial Growth Factor (VEGF).

In a presently preferred embodiment, the jacket is impregnated with a liquid containing the therapeutic or diagnostic agent. For example, a jacket formed from heterologous tissue which is submerged in a solution of the therapeutic agent will absorb the solution. A variety of suitable methods of applying the agent to the jacket may be used, including using electrodeposition, heat and pressure. Thereafter, the stent assembly can be positioned at a desired site within the patient's body lumen, where the jacket will release the therapeutic agent. The jacket on the stent assembly may be impregnated just before use, or alternatively, stored in the therapeutic or diagnostic agent so that the stent assembly is preimpregnated.

The invention is also directed to a method for delivery of a therapeutic or diagnostic agent within a body lumen. The stent assembly including a tubular stent with a jacket of biocompatible, non-thrombogenic expandable material, such as heterologous tissue, containing a therapeutic or diagnostic agent is positioned within the body lumen as outlined above. With the stent assembly positioned at a desired location, the therapeutic or diagnostic agent is released from the jacket into the body lumen and thereby delivered at and around the location of the stent assembly within the body lumen.

The expanded jacket of biocompatible, non-thrombogenic expandable material such as heterologous tissue should extend over a substantial portion, preferably all, of the stenotic region in which it is disposed in order to minimize the restenosis.

DETAILED DESCRIPTION OF THE INVENTION

Figure 1:
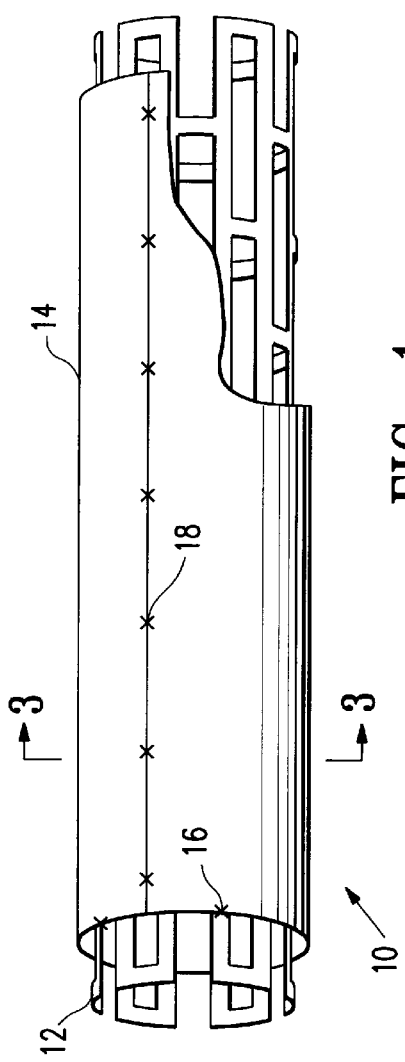
FIG. 1 is a perspective view, partially broken away, of a stent assembly of the invention showing a tubular, expandable stent with an expandable biocompatible non-thrombogenic cylindrical exterior jacket.

In the embodiment of the invention shown in FIG. 1, stent assembly 10 comprises a tubular, expandable metallic framework forming the stent 12 with an exterior jacket 14 of heterologous tissue. In the embodiment illustrated in FIG. 1, metallic stent 12 extends about 1 mm beyond each end of jacket 14 to prevent prolapse of the tissue into the lumen of the stent when it is expanded. Jacket 14 may be secured to metallic framework 12 by any suitable means. For example, four radially spaced sutures 16 may be placed at each end of jacket 14.

Figure 3:
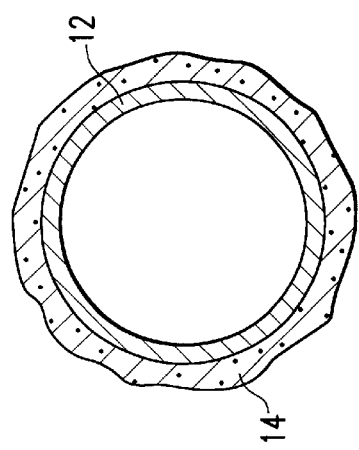
FIG. 3 is a transverse cross sectional view of the stent assembly shown in FIG. 1, taken along lines 3—3.

In a presently preferred embodiment of the stent assembly illustrated in FIG. 1, the jacket 14 contains a therapeutic or diagnostic agent, as shown in FIG. 3, illustrating a transverse cross section of the stent assembly shown in FIG. 1, taken along lines, 3—3.

Exterior jacket 14 preferably comprises bovine pericardium, a material shown to resist suture line bleeding, require no pre-clotting, support endothelialization and have an excellent host-tissue response. Further, bovine pericardial tissue has an elasticity of up to about 30% which allows the tissue cylinder to conform to both the unexpanded and expanded configurations of the stent 12 with out adding a great deal of bulk which increases the profile on the balloon. Other heterologous tissue suitable in the practice of the invention includes porcine pericardium, aortic leaflet, veins and arteries, and others. Useful heterologous tissue is relatively impervious and impenetrable so as to prevent tissue build up and the migration of smooth muscle cells through the stent framework. A particularly preferred bovine pericardium has cross-linked collagen and is available from Bio Vascular. Bovine pericardium tissue is available in a thickness ranging from about 0.25 mm to about 0.75 mm, with an average of about 0.45 mm.

In a presently preferred embodiment of the invention, the biocompatible non-thrombogenic jacket 14 has a thickness of less than about 0.25 mm, and preferably has a thickness of about 0.05 mm to about 0.20 mm, and most preferably about 0.1 mm to about 0.15 mm. However, biocompatible non-thrombogenic jackets having a thickness of up to about 0.75 mm may be used. In the embodiment of the invention in which a thin biocompatible non-thrombogenic jacket having a thickness of less than about 0.25 mm is used, the heterologous tissue used to form the jacket is typically thinned before being assembled with the stent. The tissue may be thinned by a variety of suitable methods including peeling, shaving or otherwise removing a thin layer of the tissue. In a presently preferred embodiment, the thin jacket comprises the serous pericardium, which is the smooth, inner layer of the pericardium, which has been separated from at least a part of the outer layer of the pericardium. Similarly, where other forms of heterologous tissue are used, such as veins or arteries, the venous or arterial walls may be thinned to the presently preferred thickness of about 0.05 mm to about 0.20 mm. As a result of being thinned, the jacket may have reduced elasticity, so that the thin jacket is preferably provided on the unexpanded stent in a folded or overlapping wrapped configuration which provides sufficient material to cover the larger circumference of the expanded stent, as will be discussed in greater detail below.

Figure 4:
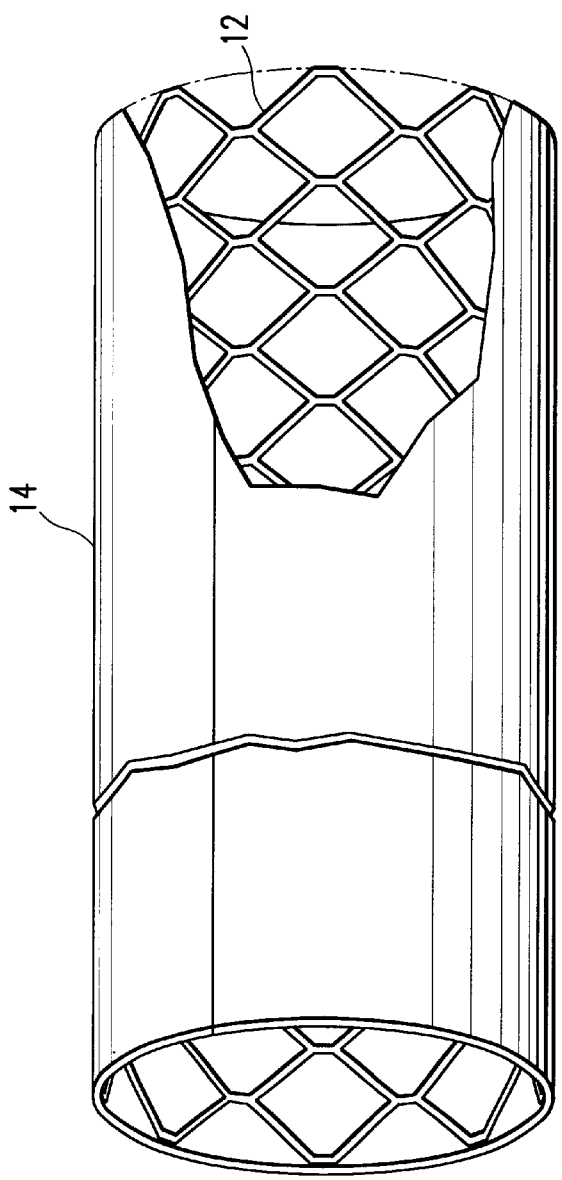
FIG. 4 is a perspective view, partially in section, of one embodiment of the stent assembly, shown in the expanded configuration, having a biocompatible non-thrombogenic jacket covering the length of the expandable stent.

The biocompatible non-thrombogenic jacket 14 preferably has a length configured to cover the length of the expanded stent, as illustrated in FIG. 4, showing an expanded stent 12 with a jacket 14 extending the length of the stent, with a length equal to the stent length. However, the jacket may have a length that is not equal to the length of the stent. For example, the jacket may have a length less than the stent length, as illustrated in FIG. 1, preferably not more than about 10%–20% less than the length of the stent. However, the jacket may cover an even smaller percentage of the length of the stent, as for example, when the stent assembly is used in a Transjugular Intrahepatic Portal Shunt (TIPS) application, where the jacket length is about 50% less than the length of the stent. Alternatively, the jacket may have a length greater than the length of the stent, preferably not more than about 5% greater than the stent length. The jacket preferably has a circumference about equal to the circumference of the expanded stent, configured to fit on an inner or outer surface of the expanded stent. The jacket preferably fits on the expanded stent so that the jacket conforms to the expanded stent without flaps of excess material.

Metallic stent 12 may comprise any suitable conventional stent. For example, Micro Stent II and GFX stents available from Arterial Vascular Engineering, and Multi-Link, available from Guidant, have proven useful. Other stents that may be used in the practice of this invention include the Palmaz-Shatz stent from Johnson and Johnson, the Gianturco stent from Cook Incorporated and other commercially available stents. Conventional balloon expandable stents are preferred, but, as previously mentioned, self-expanding stents, such as those formed from shape memory materials, are also suitable.

Figure 6:
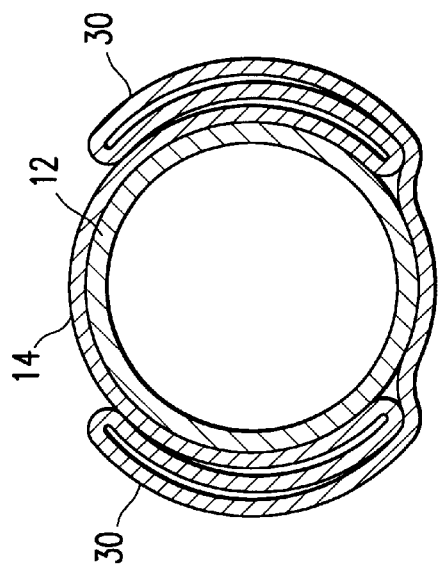
FIG. 6 is a transverse cross sectional view of another embodiment of the stent assembly prior to being expanded, illustrating the biocompatible non-thrombogenic jacket in a U-shaped folded configuration.
Figure 5:
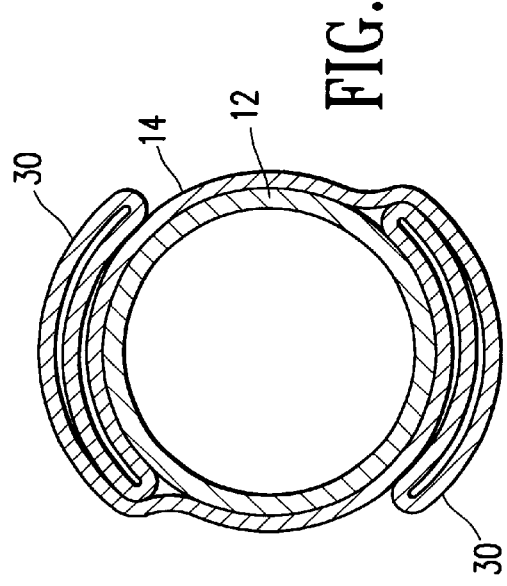
FIG. 5 is a transverse cross sectional view of one embodiment of the stent assembly prior to being expanded, illustrating the biocompatible non-thrombogenic jacket in a S-shaped folded configuration.

The stent assembly is formed by covering a surface of the unexpanded stent with the heterologous tissue forming the jacket 14. In one embodiment, the heterologous tissue is mounted onto the unexpanded stent in the form of a cylinder of tissue. The cylinder of heterologous tissue forming the jacket 14, may be formed by cutting a rectangle of tissue having a length about 2 mm shorter than the stent on which it is to be mounted and a width about equal to the circumference of the expanded stent. The two sides corresponding to the length of the stent then may be secured together, such as by sewing with 6-0, 7-0, 8-0 or 10-0 polypropylene sutures. Other means for securing the sides of the stent cover together include mechanical means such as staples, adhesive or chemical bonding and the like. It may be desirable to support the tissue while manipulating it. For example, a 9 French introducer dilator may be used to support a 3 mm diameter cylinder, an 11 French dilator for a 3.5 mm cylinder and a 12 French dilator for a 4 mm cylinder. The cylinder of tissue having a circumference about equal to the circumference of the expanded stent may be provided on the unexpanded stent in a folded or wrapped configuration. In one embodiment, the tissue on the unexpanded stent forms wings 30 on either side of the stent which are folded about stent, reducing the profile of the assembly, and unfolding upor expansion of the stent. In the embodiment illustrated in FIG. 5, the wings are folded in the same direction in an S-shaped configuration. In another embodiment, illustrated in FIG. 6, the wings of the cylinder of tissue on the unexpanded stent are folded about stent in opposite directions in a U-shaped configuration. However, the cylinder of tissue may be placed about the unexpanded stent in a variety of suitable configurations, as for example, where the wings of the cylinder of tissue are collapsed toward the stent, such as in an accordion type configuration (not shown). It would be apparent to one of skill in the art that the heterologous tissue forming the jacket could be folded about the unexpanded stent as outlined above whether or not the tissue had been formed into a cylinder of tissue before mounting onto the unexpanded stent.

Figure 7:
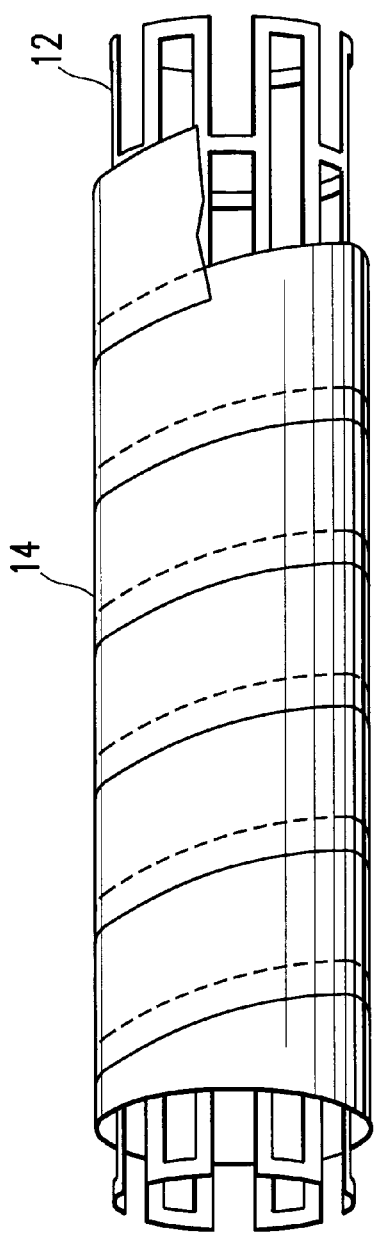
FIG. 7 is a perspective view, partially broken away, of one embodiment of the stent assembly having a biocompatible non-thrombogenic jacket comprising an overlapping ribbon.
Figure 8:
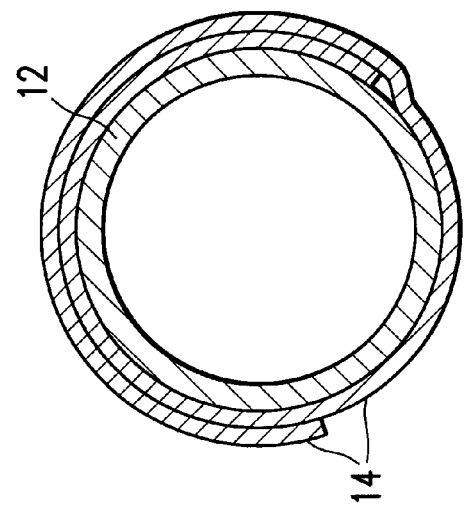
FIG. 8 is transverse cross sectional view of one embodiment of the stent assembly prior to being expanded, having a biocompatible non-thrombogenic jacket in an overlapping wrapped configuration.

In another embodiment, the heterologous tissue is wrapped around the unexpanded stent, so that sufficient tissue to cover the expanded stent is provided. In one embodiment, illustrated in FIG. 7, a ribbon of tissue is spirally wrapped around the unexpanded stent down a length thereof. The adjacent turns of the ribbon of tissue overlap, so that the ribbon unwraps as the stent expands to provide the jacket 14 configured to cover the expanded stent and having a circumference about equal to the circumference of the expanded stent. Preferably, the ribbon of tissue is wrapped along the entire length of the stent. In another embodiment, a rectangle of tissue having a width about equal to the circumference of the expanded stent on which it is to be mounted is repeatably wrapped around the outer circumference of the unexpanded stent, so that multiple layers of tissue are present on at least a part of the unexpanded stent, as shown in FIG. 8, illustrating a transverse cross section of an unexpanded stent with a wrapped jacket thereon. Preferably, one end of the tissue is fixed to the stent, and the tissue is then tightly wrapped around the stent. Upon expansion of the stent, the tissue unwraps to provide the jacket 14 having a circumference about equal to the circumference of the expanded stent. Preferably the length of the tissue is about equal to the length of the stent.

The tissue can be caused to remain in the folded or wrapped configurations until the stent is expanded by pressing the fluid out of the folded or wrapped tissue. Additionally, securing members such as surgical tape, ties, or breakable bands may be provided to releasably hold the tissue in the folded or wrapped configurations.

Depending upon the jacket material, the tissue may be kept wet at all times during manipulation or it may be dry until advanced into the patient's blood stream. Additionally, radio-opaque markers, such as rings of gold or platinum, may be added to the outer layer of the tissue so that the integrity of the cylinder may be assured before deployment within the body lumen. The cylinder of heterologous tissue configured to be mounted onto a stent and the jacket 14 formed by the cylinder of tissue or the unwrapped or unfolded tissue generally has a length, for coronary applications, of about 4 to greater than about 80 mm, typically about 5 to about 80 mm, preferably about 10 to about 50 mm, and a diameter of about 1.5 to about 35 mm, typically about 2 to about 6 mm, preferably about 2.5 to about 5 mm. The actual length and diameter of the cylinder of heterologous tissue may vary, and will depend on the nature of the vessel in which the stent assembly is implanted. For example, for peripheral vessel applications, such as an aortic abdominal aneurysm, a larger cylinder of heterologous tissue having a length of about 5 mm to about 200 mm and a diameter of about 2 mm to about 60 mm would be used.

Figure 2:
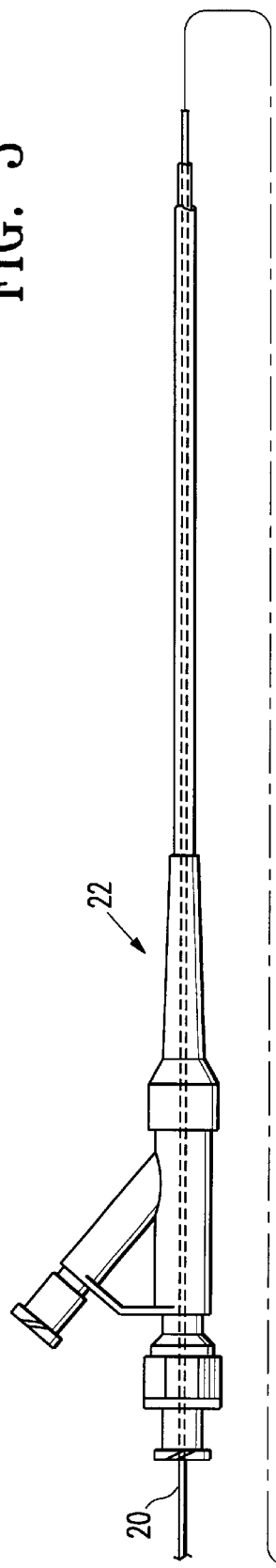
FIG. 2 is an elevational view, partially in section, of a delivery catheter having a jacketed stent mounted on an inflatable balloon on the distal extremity of the catheter.

The jacketed stent assembly 10 is inserted into the body lumen in the following fashion. A guidewire 20 is back-loaded into a delivery catheter 22 having the jacketed stent assembly 10 mounted over an inflatable balloon 24 on the distal extremity of the delivery catheter (as schematically shown in FIG. 2) or on a self expanding stent delivery system (not shown). The catheter 22 and guidewire 20 are percutaneously introduced by means of a conventional Seldinger technique and a 5–9 or 10 French guiding catheter (not shown) into the patient's arterial system. Larger guiding catheters, for example up to about 25 Fr, may be used depending on the application. The guidewire 20 is advanced out delivery catheter 22 through the vasculature under fluoroscopic imaging until it crosses a stenotic region. Then the catheter 22 is advanced over the guidewire 20 until the stent assembly 10 is positioned at the desired location within the stenotic region. Then, the balloon 24 is inflated or the securing mechanism of the self expanding stent is released to expand the stent 12 and cylindrical jacket 14, seating the assembly 10 within the vessel. The balloon 24 is then deflated and the catheter 22 is removed, leaving the expanded stent assembly 10 in place.

Although primarily described with respect to preventing restenosis in angioplasty patients, the covered stents of this invention may be used in a number of coronary artery, peripheral artery and non-vascular applications. For example, coronary artery applications include use in ectatic arteries and ectatic arteries containing an obstructive lesion, aneurismatic arteries, saphenous vein grafts and native arteries, coronary perforation, coronary fistula, and ostial coronary lesions. Peripheral artery applications include aortic abdominal aneurysm and other aneurismatic peripheral arteries, transjugular intrahepatic portal shunt, percutaneous transluminal angioplasty, fistula closing and neuro interventions (such as aneurysms and arterial-venous malformations), small vessel intraluminal grafting, and ostial renal artery lesions. Finally, the covered stents of this invention may be used in urological, gastroenterological, respiratory, neurological, and other non-vascular applications. For example, urological field applications include urethral stenting for stenosis due to tumors, fibrous tissue and perforation. Gastroenterological field applications include fistula closing, reconstruction such as esophagus reconstruction, and esophageal bleeding. Respiratory field applications include tracheal and bronchial obstructions, and neurological field applications include carotid angioplasty.

A general description of the device of the present invention as well as a preferred embodiment of the present invention has been set forth above. One skilled in the art will recognize and be able to practice many changes in many aspects of the device described above, including variations that fall within the teachings of this invention. For example, the assembly may include a second expandable stent, so that the heterologous tissue layer is between two coaxially disposed stents. Additionally, the jacket may cover the entire stent or only a portion thereof. Additionally, the stent assembly may be used in branched body lumens, and positioned to block one or more of the branch lumens. The spirit and scope of the invention should be limited only as set forth in the claims which follow.

What is claimed is:

1. A stent assembly for maintaining the patency of a body lumen comprising an expandable stent with a cylindrical jacket formed of biocompatible, non-thrombogenic material, the cylindrical jacket comprising a thinned layer of pericardium having a cut surface formed by removal of an outer layer of the pericardium, wherein the cylindrical jacket is serous pericardium separated from the outer layer of pericardium.

2. The stent of claim 1, wherein the pericardium is selected from the group consisting of bovine pericardium, and porcine pericardium.

3. The stent of claim 2, wherein the pericardium comprises bovine pericardium with cross-linked collagen.

4. The stent of claim 1 including at least one therapeutic or diagnostic agent releasably contained in the cylindrical jacket.

5. The stent assembly of claim 1 wherein the material is expandable.

6. The stent assembly of claim 1 wherein the stent comprises a metallic tubular member.

7. The stent assembly of claim 1 wherein the stent is disposed within the cylindrical jacket.

8. A method for maintaining the patency of a body lumen comprising the steps of:

a) mounting on a delivery catheter a stent assembly comprising a tubular expandable stent with a cylindrical jacket formed of biocompatible, non-thrombogenic expandable material, the cylindrical jacket comprising a thinned layer of pericardium having a cut surface formed by removal of an outer layer of the pericardium, wherein the cylindrical jacket is serous pericardium separated from the outer layer of pericardium;

b) advancing the delivery catheter through the body lumen until the stent assembly is positioned at a desired location;

c) expanding the stent assembly to anchor it within the body lumen; and d) withdrawing the delivery catheter.

9. A cylindrical jacket configured to fit over a portion of an intraluminal stent comprising a thinned layer of pericardium having a cut surface formed by removal of an outer layer of the pericardium, wherein the cylindrical jacket is serous pericardium separated from the outer layer of pericardium.

10. The cylindrical jacket of claim 9 having a length of about 4 to about 200 mm.

11. The cylindrical jacket of claim 9 having a length of about 10 to about 50 mm.

12. The cylindrical jacket of claim 9 having a diameter of about 1.5 to about 60 mm.

13. The cylindrical jacket of claim 12 having a diameter of not greater than about 6 mm.

14. The cylindrical jacket of claim 9 having a diameter of about 2.5 to about 5 mm.

15. The cylindrical jacket of claim 9 having a thickness of about 0.05 mm to about 0.20 mm.

16. The cylindrical jacket of claim 9 having a thickness of about 0.1 mm to about 0.15 mm.

17. The cylindrical jacket of claim 9 configured to fit over an outer portion of the intraluminal stent.

18. The cylindrical jacket of claim 9 configured to cover an inner portion of the intraluminal stent.

19. An expandable jacketed stent comprising a metallic tubular member configured to expand from a first circumference to a second circumference, and a jacket formed of heterologous tissue on an outer surface of the stent in a folded configuration configured to unfold as the stent expands to the second circumference, wherein the jacket has a circumference on the unexpanded stent larger than the first circumference of the stent, and a circumference on the expanded stent about equal to the second circumference of the stent.

20. A method of treating a patient, comprising:

a) providing an elongated delivery catheter having an expandable member on a distal extremity thereof;

b) mounting onto the expandable member on the distal extremity of the delivery catheter an expandable stent configured to expand from a first circumference to a second expanded circumference and having a cylindrical jacket formed of biocompatible, non-thrombogenic expandable material on an outer surface of the stent in a folded configuration having at least one wing configured to unfold as the stent expands to the second circumference, wherein the jacket has a circumference on the unexpanded stent larger than the first circumference of the stent, and a circumference on the expanded stent about equal to the second expanded circumference of the stent;

c) advancing at least the distal extremity of the catheter within a body lumen of the patient until the jacketed stent is disposed at a desired location within the body lumen;

d) expanding the expandable member on the distal extremity of the catheter to expand the jacketed stent mounted thereon and unfold the jacket wing as the stent expands to the second circumference, and fix the expanded jacketed stent within the body lumen; and e) contracting the expanded expandable member so the elongated delivery catheter can be removed from the patient.

21. The stent assembly of claim 1, wherein the cylindrical jacket has a length less than a length of the stent.

22. The stent assembly of claim 1, wherein the cylindrical jacket has a length greater than a length of the stent, the length of the cylindrical jacket being not more than 5% greater than the length of the stent.

23. The stent assembly of claim 1, wherein the stent is expandable from an unexpanded configuration to an expanded configuration, and wherein the cylindrical jacket on the unexpanded stent has a circumference larger than a circumference of the stent in the unexpanded configuration, and about equal to a circumference of the stent in the expanded configuration.

24. The jacketed stent of claim 19 wherein the jacket in the folded configuration on the unexpanded stent has at least one wing configured to unfold upon expansion of the stent to the second circumference.

25. The jacketed stent of claim 24 wherein the jacket has wings on opposite sides of and folded about the unexpanded stent.

26. The jacketed stent of claim 25 wherein the wings are folded in the same direction into an S-shaped configuration.

27. The jacketed stent of claim 25 wherein the wings are folded in opposite directions into a U-shaped configuration.

28. The jacketed stent of claim 24 including at least one securing member releasably fixing the wing prior to expansion of the stent.

29. The jacket stent of claim 19, wherein the jacket is a thinned layer of tissue having a thickness of about 0.05 mm to about 0.20 mm.

30. The method of claim 20 including removing fluid out of the jacket after (b) and prior to (c).

31. The method of claim 10 including before (a) removing an outer layer of tissue from the pericardium to form the thinned layer of pericardium.

32. A method of treating a patient, comprising:

a) providing an elongated delivery catheter having an expandable member on a distal extremity thereof;

b) mounting onto the expandable member on the distal extremity of the delivery catheter an expandable stent configured to expand from a first circumference to a second expanded circumference and having a cylindrical jacket formed of biocompatible, non-thrombogenic expandable material on an outer surface of the stent, wherein the jacket on the unexpanded stent has a circumference larger than the first circumference of the stent, and about equal to the second expanded circumference of the stent;

c) removing fluid out of the jacket after (b), and thereafter advancing at least the distal extremity of the catheter within a body lumen of the patient until the jacketed stent is disposed at a desired location within the body lumen;

d) expanding the expandable member on the distal extremity of the catheter to expand the jacketed stent mounted thereon and fix the expanded jacketed stent within the body lumen; and e) contracting the expanded expandable member so the elongated delivery catheter can be removed from the patient.

\* \* \* \* \*

UNITED STATES PATENT AND TRADEMARK OFFICE
CERTIFICATE OF CORRECTION

PATENT NO. : 6,254,627 B1
DATED : July 3, 2001
INVENTOR(S) : Carlos Vonderwalde Freidberg It is certified that error appears in the above-identified patent and that said Letters Patent is hereby corrected as shown below:

Column 8,
Line 40, change "stert" to -- stent --.

Column 10,
Line 6, change "10" to -- 8 --.

Signed and Sealed this

Twenty-first Day of May, 2002

Attest:

JAMES E. ROGAN
*Director of the United States Patent and Trademark Office*

*Attesting Officer*